(12) United States Patent
Chang et al.

(10) Patent No.: US 6,635,654 B1
(45) Date of Patent: Oct. 21, 2003

(54) OPHTHALMIC COMPOSITIONS CONTAINING LORATADINE

(75) Inventors: Chin-Ming Chang, Tustin, TX (US); Eldon Q. Farnes, Laguna Beach, CA (US); Orest Olejnik, Coto De Caza, CA (US); James N. Chang, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/340,355

(22) Filed: Jan. 9, 2003

(51) Int. Cl.$^7$ ............................................. A61K 31/44
(52) U.S. Cl. ...................................... 514/290
(58) Field of Search ......................... 514/290

(56) References Cited

U.S. PATENT DOCUMENTS

| | | |
|---|---|---|
| 4,282,233 A | 8/1981 | Vilani |
| 5,441,958 A | 8/1995 | Yanni et al. |
| 5,496,811 A | 3/1996 | Aviv et al. |
| 5,578,586 A | 11/1996 | Glonek et al. |
| 5,668,133 A | 9/1997 | Yanni et al. |
| 5,981,607 A | 11/1999 | Ding et al. |
| 6,132,758 A | 10/2000 | Munayyer et al. |
| 6,267,985 B1 | 7/2001 | Chen et al. |
| 6,495,160 B2 | 12/2002 | Esposito et al. |
| 2002/0032171 A1 | 3/2002 | Chen et al. |
| 2002/0034539 A1 | 3/2002 | Esposito et al. |
| 2002/0107265 A1 * | 8/2002 | Chen et al. ................. 514/310 |

FOREIGN PATENT DOCUMENTS

| | | |
|---|---|---|
| EP | 0028110 A2 | 5/1981 |
| EP | 0433766 A1 | 6/1991 |
| EP | 0480690 A1 | 4/1992 |
| EP | 0759773 B1 | 3/1997 |
| EP | 0 872 236 A1 * | 10/1998 |
| EP | 0 978 281 A1 * | 2/2000 |
| EP | 10446781 | 10/2000 |
| WO | WO 97/15307 | 5/1997 |
| WO | WO 98/48803 | 11/1998 |
| WO | WO 99/62516 | 12/1999 |
| WO | WO 01/89527 | 11/2001 |

OTHER PUBLICATIONS

Ableson, M.B., et al., *Effects of Topically applied ocular decongestant and antihistamine*, American Journal of Ophthalmology, 90:254–257, 1980.

Abelson, M.B., *Evaluation of olopatadine, a new ophthalmic antiallergic agent with dual activity, using the conjunctival allergen challenge model*, Ann Allergy Asthma Immunol 1998:81:211–218.

Berdy, G.J., et al., *Allergic Conjunctivitis: a survey of New antihistamines*, vol. 7, No. 4, 1991: Mary Ann Liebert, Inc. Publishers., pp. 313–324.

Dechant, K.L., et al., *Levocabastine, A review of its pharmacological properties and therapeutic potential as a topical antihistamine in allergic rhinitis and conjunctivitis* Drugs 1991: 41 (2): 202–24.

Doughty, M.J.., *Levocabastine, a topical ocular antihistamine available as a pharmacy medicine–a literature review*, The Pharmaceutical Journal, vol. 268, Mar. 16, 2002, pp. 367–370.

Miller, J., et al., *Antazoline phosphate and naphazoline hydrochloride, singly and in combination for the treatment of allergic conjunctivitis–a controlled double–blind clinical trial*, Annals of Allergy, Antazoline Phosphate, vol. 35, Aug. 1975, pp. 81–86.

Vandewalker, M. L., et al., Abstract, *Efficacy of vasocon–a–and its components with conjunctival provocation testing (CPT)*, #523 (No date available).

Internet Article: Medem, Inc. *Eye Allergies and Allergic Conjunctivitis*, Medical Library: Eye Allergies and Allergic Conjunctivitis, American College of Allergy, Asthma & Immunology–www.medem.com/medlb/article detaillb for printer.cfm, printed Dec. 9, 2002, 4 pgs.

Internet Article: *Allergic Conjunctivitis*, http;://familydoctor.org/handounts/678.html printed Dec. 9, 2002 printed Dec. 9, 2002, 2 pgs, American Academy of Family Physicians.

Internet Article: Review of Optometry, *Ocular Allergy Treatment Drugs*, May 15, 2002, www.revoptom.com/drugguide.asp?show =view& articleid +4, printed Dec. 9, 2002, 6 pgs.

* cited by examiner

*Primary Examiner*—Raymond Henley, III
(74) *Attorney, Agent, or Firm*—Brent A. Johnson; Martin A. Voet; Robert J. Baran

(57) ABSTRACT

The present invention is directed to an ophthalmic formulation which comprises a therapeutically effective amount of ethyl 4-(8-chloro-5,6-dihydro-11-benzo[5,6]cyclohepta[1,2-b]pyridin-11-ylidene)-1-piperidinecarboxylate, known as loratadine, a fatty acid ester, and a surfactant, which has been found to be useful in treating ocular allergies, especially allergic conjunctivitis, and related conditions.

24 Claims, No Drawings

OPHTHALMIC COMPOSITIONS CONTAINING LORATADINE

FIELD OF THE INVENTION

The present invention relates to a pharmaceutical composition for relieving ocular allergies. More particularly, the present invention relates to ophthalmic compositions comprising ethyl 4-(8-chloro-5,6-dihydro-11-benzo[5,6]cyclohepta[1,2-b]pyridin-11-ylidene)-1-piperidinecarboxylate, otherwise known as loratadine.

BACKGROUND OF THE INVENTION

Allergic conjunctivitis is an ocular allergy characterized by redness, itching and swelling of the eyes. Allergic conjunctivitis is a similar reaction to allergies of the sinuses, nose, or lungs, in that it is characterized by the release of histamines from contact with allergens such as pollen, pet hair or dander, or dust. $H_1$ histamine receptor antagonists are used widely in the systemic treatment of allergies, and have recently been shown to be effective when used topically on the eye. (Doughty, The Pharmaceutical Journal, 268, 367–370, Mar. 16, 2002). Two $H_1$ histamine receptors, emedastine and levocabastine, are currently available in eye drop formulations for treatment of allergic conjunctivitis and related conditions. Another $H_1$ histamine receptor, Loratadine, sold by Schering-Plough under the brand name Claritin®, is used widely in the oral dosages forms of tablets and syrup for the systemic treatment of allergies. However, no topical ophthalmic product containing loratadine is currently available due to its insolubility and instability in aqueous solutions. The low water solubility of loratadine results in poor delivery of the drug topically, resulting in limited ocular activity. For water insoluble active agents such as loratadine, ophthalmic formulations typically comprise a suspension or a solution containing solubilizers such as surfactants, cosolvents and complexing agents to enhance the solubility of the compound.

The manufacturer of Claritin®, Schering-Plough, has experimentally prepared an ophthalmic formulation of loratadine using Tween-80®, a surfactant, as a solubilizer. (WO9715307) This formulation required at least 2.3% Tween-80® to solubilize 0.05% loratadine in solution. However, the relatively high concentration of surfactant increases eye irritation, which is counterproductive in a product intended to reduce ocular discomfort and irritation. Claritin® syrup is formulated at pH 2.5–3.1, at which pH loratadine is more soluble. However, this acidic pH is not suitable for ophthalmic liquids. In addition to being less soluble at the desirable ophthalmic pH range of 6–8, loratadine is also chemically unstable at this pH range. The cleavage of the ester linkage leads to the formation of the corresponding acid and ethyl alcohol much more readily in neutral or basic aqueous solutions.

Schering-Plough also formulated eye drops containing loratadine metabolites or derivatives that had some improved properties (WO 9848803). However, despite these efforts, no topical ophthalmic product containing loratadine as the active ingredient is currently available, although the patent for loratadine (U.S. Pat. No. 4,282,233) issued in 1981. Given the importance of loratadine in treating systemic allergies, one skilled in the art would expect that a topical ophthalmic product containing loratadine would also make a significant contribution to the treatment of ocular allergies. The lack of an available topical ophthalmic product containing loratadine therefore shows that difficulties in formulating loratadine have not been overcome, and that a need still exists to formulate the compound into effective topical ophthalmic product.

SUMMARY OF THE INVENTION

DETAILED DESCRIPTION OF THE INVENTION

Unexpectedly, we have found that the difficulties experienced by others in formulating loratadine are overcome by the present invention, which delivers loratadine in an aqueous ophthalmic emulsion composition. In the present invention, the loratadine is dissolved in the oil phase of an oil-in-water emulsion system. This confers three main advantages to this invention over previous topical ophthalmic loratadine products. These advantages are higher drug absorption, minimal decomposition of loratadine by hydrolysis, and lubrication and improved comfort to the eye.

We have found that the solubility of loratadine in vegetable oils is great enough to formulate an effective amount of the agent into an ophthalmic emulsion formulation (see Table 1) to be used for allergic conjunctivitis and

TABLE 1

Solubility of Loratadine in Vegetable Oils

| Oil | Solubility (mg/mL) |
| --- | --- |
| Castor Oil | 85 |
| Corn Oil | 25 |
| Miglyol 810N | 15 |
| Peanut Oil | 15 |
| Sesame Oil | 15 |
| Soybean Oil | 15 |
| Polysorbate 80 (Nonionic surfactant) | 25 | related conditions. The solubility of loratadine in vegetable oils is comparable to or better than its solubility in a surfactant. In particular, castor oil dissolves more than three times as much loratadine as Polysorbate 80, a commonly used surfactant in ophthalmic solutions. By contrast to the irritation to the eye caused by the surfactant alone, it has been shown in commonly assigned U.S. Pat. No. 5,668,133, incorporated herein by reference, that an emulsion actually provides lubrication and improved comfort to the eye. It has also been shown, in European Patent No. 1044678, that an emulsion of vegetable oil and water delivers a higher concentration of the drug cyclosporin A to the conjunctiva of a rabbit eye than the individual oil. Additionally, dissolving the hydrophobic loratadine in the oil phase of an emulsion significantly reduces the contact of the hydrophobic loratadine with water, enabling a formulation to be prepared in the ophthalmically useful pH range of 6–8. This is in contrast with aqueous solutions where the loratadine is readily hydrolyzed in the desired ophthalmic pH range, greatly reducing the activity and the shelf life of the product.

The present invention is directed to an ophthalmic formulation which comprises a therapeutically effective amount of loratadine, a fatty acid ester, and a surfactant. In the preferred embodiment of this invention, the fatty acid ester is a vegetable oil. A fatty acid ester has the meaning commonly understood in the art, being an ester formed between an alcohol and a fatty acid. While not intending to limit the scope of this invention, some examples of readily available fatty acid esters are triglyceride esters commonly known as vegetable oils, mono and diglyceride esters of fatty acids, and fatty acid methyl esters. The fatty acid ester may be a mixture of several chemical compounds or an essentially pure compound. Preferably, the fatty acid ester is a vegetable oil. Examples of vegetable oils include castor oil, sesame oil, soybean oil, cottonseed oil, olive oil, peanut oil, safflower oil, sunflower oil, palm oil, palm kernel oil, canola oil, and Miglyol oil. Most preferably, the fatty acid ester is castor oil.

The determination of a therapeutically effective amount of loratadine used in this formulation can be readily determined by one skilled in the art. Preferably, the concentration of loratadine is between about 0.01% and about 1.5%. More preferably, the concentration of loratadine is about 0.0125% or about 0.0625%.

The term surfactant used in this invention has the meaning commonly understood in the art. Surfactants are used to both help facilitate the formation of the emulsion and improve its stability. Anionic, cationic, amphoteric, zwitterionic, and nonionic surfactants may all be used in this invention. Preferably, a nonionic surfactant is used in this invention. While not intending to limit the scope of the invention, some examples of useful nonionic surfactants are polysorbates, poloxamers, alcohol ethoxylates, ethylene glycol-propylene glycol block copolymers, fatty acid amides, alkylphenol ethoxylates, and phospholipids. Most preferably, Polysorbate 80 is used as the surfactant. Polysorbate 80 is a mixture of oleate esters of sorbitol and sorbitol anhydrides, consisting predominantly of the monoester, condensed with approximately 20 moles of ethylene oxide. It conforms generally to the formula:

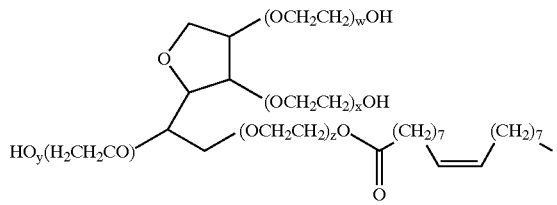

where w+x+y+z has an average value of 20. Polysorbate 80 is available from ICI Americas, Inc., Wilmington, Del.

In another preferred embodiment of this invention, an emulsion stabilizing polymer is used. While not intending to limit the scope of the invention, emulsion stabilizing polymers generally contain hydrophilic groups such as cellulose, sugars, ethylene oxide, hydroxide, carboxylic acids or other polyelectrolytes. While not wishing to limit the scope of the invention by theory, it is believed that these polymers help to stabilize emulsions by increasing the viscosity of the formulation as well as by reducing the interfacial tension. While not intending to limit the scope of the invention, some examples of emulsion stabilizing polymers useful in this invention are carbomers, Pemulen®, sodium carboxymethylcellulose, hydroxypropylmethylcellulose, povidone, polyvinyl alcohol, and polyethylene glycol. In the most preferred embodiment of this invention, Pemulen® is used as the polymeric based stabilizer.

Pemulen® is a registered trademark of B.F. Goodrich for polymeric emulsifiers and commercially available from B.F. Goodrich Company, Specialty Polymers & Chemicals Division, Cleveland, Ohio. Pemulens® are Acrylates/C10-30 Alkyl Acrylate Cross-Polymers. They are high molecular weight co-polymers of acrylic acid and a long chain alkyl methacrylate cross-linked with allyl ethers of pentaerythritol. They contain not less than 52.0 percent and not more than 62.0 percent of carboxylic acid groups. The viscosity of a neutralized 1.0 percent aqueous dispersion is between 9,500 and 26,500 centipoises.

In the preferred embodiment of this invention the weight ratio of castor oil to Polysorbate 80 is from about 0.3 to about 30. In a more preferred embodiment of this invention, the weight ratio is from about 0.5 to about 12.5.

In another preferred embodiment of this invention, a buffering agent is used to maintain the pH in the therapeutically useful range of about 6–8. Buffering agents used are those known to those skilled in the art, and, while not intending to be limiting, some examples are acetate, borate, carbonate, citrate, and phosphate buffers. In the most preferred embodiment of this invention, boric acid is the buffering agent.

In another preferred embodiment of this invention, a tonicity agent is used to adjust the composition of the formulation to the desired isotonic range. Tonicity agents are known to those skilled in the ophthalmic art, and, while not intending to be limiting, some examples include glycerin, mannitol, sorbitol, sodium chloride, and other electrolytes. In the most preferred embodiment of this invention, the tonicity agent is glycerin.

In another preferred embodiment of this invention, a preservative is used. Preservatives are used to prevent bacterial contamination in multiple-use ophthalmic preparations, and, while not intending to be limiting, examples include benzalkonium chloride, stabilized oxychloro complexes (otherwise known as Purite®), phenylmercuric acetate, chlorobutanol, benzyl alcohol, parabens, and thimerosal. In the most preferred embodiment of this invention, the preservative is Purite®.

In another preferred embodiment of this invention, a chelating agent is used to enhance preservative effectiveness. Suitable chelating agents are those known in the art, and, while not intending to be limiting, edetate salts like edetate disodium, edetate calcium disodium, edetate sodium, edetate trisodium, and edetate dipotassium are examples of useful preservatives.

The best mode of making and using the present invention are described in the following examples. These examples are given only to provide direction and guidance in how to make and use the invention, and are not intended to limit the scope of the invention in any way.

FORMULATION EXAMPLES

Ophthalmic Formulations 1 and 2 containing loratadine were formulated with the compositions shown in Table 2. Emulsions were prepared according to the method described in U.S. Pat. No. 5,981,607, incorporated herein by reference, with the loratadine being added to the castor oil before introducing the oil into the emulsion.

TABLE 2

Example Loratadine Emulsion Formulations

| | Amount, % w/w | | |
|---|---|---|---|
| Ingredient | Placebo | Formulation 1 | Formulation 2 |
| Loratadine | 0 | 0.0125 | 0.0625 |
| Castor Oil | 1.25 | 1.25 | 1.25 |
| Polysorbate 80 | 1.0 | 1.0 | 1.0 |
| Pemulen ® | 0.1 | 0.1 | 0.1 |
| Glycerin | 1.0 | 1.0 | 1.0 |
| Boric Acid | 0.6 | 0.6 | 0.6 |
| Purite ® 0.0075 | 0.0075 | 0.0075 | |
| Purified Water | qs. ad. 100 | qs. ad. 100 | qs. ad. 100 |

The physical stability of the example loratadine emulsion formulations was monitored and the results are provided in Table 3. The emulsions were allowed to stand for 5.5 months at 20–25° C., and the emulsion droplet sizes were measured. The emulsion droplet sizes within experimental error, were identical at 5.5 months to those measured right after the emulsions were prepared, suggesting that there was no significant coalescence of the emulsion droplets. Additionally, no creaming of the formulations or precipitation of solid loratadine was observed. These results demonstrate that the emulsions prepared in these formulations have superior physical stability.

TABLE 3

Physical Stability and Droplet Size of Loratadine Formulations

| Timepoint | Test Parameter | Placebo | Formulation 1 | Formulation 2 |
|---|---|---|---|---|
| 0 | Mean Droplet Size (micron) | 0.163 | 0.114 | 0.0987 |
|  | Mean Droplet Size (micron) | 0.121 | 0.111 | 0.0935 |
|  | Creaming | none | none | none |
| 5.5 months | Mean Droplet Size (micron) | not measured | 0.115 | 0.100 |
|  | Mean Droplet Size (micron) | not measured | 0.112 | 0.0965 |
|  | Creaming | none | none | none |

TREATMENT EXAMPLE

Several drops of Formulations 1 are administered to the eyes of a patient suffering from allergic conjunctivitis. Reduction of the symptoms becomes noticeable within one hour. The treatment is repeated one or more times daily while the condition persists.

What is claimed is:

1. An aqueous ophthalmic emulsion composition comprising a therapeutically effective amount of loratadine, a fatty acid ester and a surfactant.

2. An aqueous ophthalmic emulsion composition according to claim 1 wherein the concentration of loratadine is between about 0.01% and about 1.5%.

3. An aqueous ophthalmic emulsion composition according to claim 1 wherein the concentration of loratadine is about 0.0125% or about 0.0625%.

4. An aqueous ophthalmic emulsion composition according to claim 1 which further comprises an emulsion stabilizing polymer.

5. An aqueous ophthalmic emulsion composition according to claim 4 which further comprises a buffering agent.

6. An aqueous ophthalmic emulsion composition according to claim 5 wherein the pH of the composition is between about 6 and about 8.

7. An aqueous ophthalmic emulsion composition according to claim 6 wherein the fatty acid ester is a vegetable oil.

8. An aqueous ophthalmic emulsion composition according to claim 7 wherein the surfactant is a nonionic surfactant.

9. An aqueous ophthalmic emulsion composition according to claim 8 which further comprises a tonicity agent and a preservative.

10. An aqueous ophthalmic emulsion composition according to claim 9 which further comprises a chelating agent.

11. An aqueous ophthalmic emulsion composition according to claim 10 wherein the chelating agent is an ededate salt.

12. An aqueous ophthalmic emulsion composition according to claim 9 wherein the vegetable oil is castor oil, the surfactant is Polysorbate 80, the emulsion stabilizing polymer is Pemulen®, the tonicity agent is glycerin, the buffering agent is boric acid, and the preservative is Purite®.

13. An aqueous ophthalmic emulsion composition according to claim 12 wherein the weight ratio of castor oil to Polysorbate 80 is from about 0.3 to about 30.

14. An aqueous ophthalmic emulsion composition according to claim 12 wherein the weight ratio of castor oil to Polysorbate 80 is from about 0.5 to about 12.5.

15. An aqueous ophthalmic emulsion composition according to claim 12 wherein the concentration of castor oil is about 1.25%, the concentration of Polysorbate 80 is about 1.0%, the concentration of Pemulen® is about 0.1%, the concentration of glycerin is about 1.0%, the concentration of boric acid is about 0.6%, and the concentration of Purite® is about 0.0075%.

16. An aqueous ophthalmic emulsion composition according to claim 15 wherein the concentration of loratadine is between about 0.01% and about 1.5%.

17. An aqueous ophthalmic emulsion composition according to claim 15 wherein the concentration of loratadine is about 0.0125% or about 0.0625%.

18. A method of treating ocular allergies in an affected person comprising administering to the eye of the affected person and effective amount of an aqueous ophthalmic emulsion composition comprising a therapeutically effective amount of loratadine, a fatty acid ester and a surfactant.

19. The method of claim 18 wherein the fatty acid ester is a vegetable oil and the surfactant is a nonionic surfactant.

20. The method of claim 19 wherein said aqueous ophthalmic emulsion composition further comprises an emulsion stabilizing polymer, a buffering agent, a tonicity agent, and a preservative; and wherein the pH of said ophthalmic emulsion composition is between about 6 and about 8.

21. The method of claim 20 wherein the vegetable oil is castor oil, the surfactant is Polysorbate 80, the emulsion stabilizing polymer is Pemulen®, the tonicity agent is glycerin, the buffering agent is boric acid, and the preservative is Purite®.

22. The method of claim 21 wherein the concentration of loratadine is between about 0.01% and about 1.5%.

23. The method of claim 22 wherein the concentration of castor oil is about 1.25%, the concentration of Polysorbate 80 is about 1.0%, the concentration of Pemulen® is about 0.1%, the concentration of glycerin is about 1.0%, the concentration of boric acid is about 0.6%, and the concentration of Purite® is about 0.0075%.

24. The method of claim 23 wherein the concentration of loratadine is about 0.0125% or about 0.0625%.

* * * * *

UNITED STATES PATENT AND TRADEMARK OFFICE
CERTIFICATE OF CORRECTION

PATENT NO. : 6,635,654 B1
DATED : October 21, 2003
INVENTOR(S) : Chang et al.

It is certified that error appears in the above-identified patent and that said Letters Patent is hereby corrected as shown below:

<u>Title page,</u>
Item [75], Inventors, the state of residence for the first inventor, "TX" is replaced with -- CA --

<u>Column 4,</u>
Line 63, Table 2, under the column labeled "Ingredient", "Purite® 0.0075" is replaced with -- Purite® --
Line 63, Table 2, under the column labeled "Formulation 2", the empty entry is replaced with -- 0.0075 --
Line 32, "and" is replaced with -- an --

Signed and Sealed this

Twenty-seventh Day of January, 2004

JON W. DUDAS
*Acting Director of the United States Patent and Trademark Office*